United States Patent [19]

Bulten et al.

[11] 4,431,666
[45] Feb. 14, 1984

[54] PLATINUM(IV)-DIAMINE COMPLEXES, A PROCESS FOR THE PREPARATION THEREOF, A PROCESS FOR THE PREPARATION OF A MEDICINE USING SUCH A PLATINUM(IV)-DIAMINE COMPLEX FOR THE TREATMENT OF MALIGNANT TUMORS IN MICE

[75] Inventors: Eric J. Bulten, Bilthoven; Francois Verbeek, Harmelen, both of Netherlands

[73] Assignee: Nederlandse Centrale Organisatie Voor Toegepast Natuurwelenschappelyk onderzoek, The Hague, Netherlands

[21] Appl. No.: 232,298

[22] Filed: Feb. 6, 1981

Related U.S. Application Data

[63] Continuation-in-part of Ser. No. 213,065, Dec. 4, 1980, abandoned.

[30] Foreign Application Priority Data

Mar. 1, 1980 [NL] Netherlands .......................... 8000032

[51] Int. Cl.$^3$ ...................... C07F 15/00; A61K 31/28
[52] U.S. Cl. ................................. 424/287; 260/429 R
[58] Field of Search ..................... 260/429 R; 424/287

[56] References Cited

U.S. PATENT DOCUMENTS 4,053,587 10/1977 Davidson et al. ................... 424/131
4,119,654 10/1978 Tobe et al. ...................... 260/429 R
4,140,707 2/1979 Cleare et al. .................... 260/429 R
4,228,090 10/1980 Hydes et al. ..................... 260/429 R
4,250,189 2/1981 Hydes et al. ................. 260/429 R X

OTHER PUBLICATIONS

Braddock et al., Chemico–Biological Interactions, vol. 11, No. 3, pp. 158–159 (1975).
Van Kralingen, C. G., Antitumor Platinum Compounds; Synthesis, Structure and Biological Activity, No. 7, 1979.
B. Rosenberg and L. Van Camp, Cancer Research 30 (1970) 1799–1802.
A. P. Zipp and S. G. Zipp, J. Chem. Ed., 54 (12) (1977) p. 739.
M. L. Tobe and A. R. Khokhar, J. Clinical Hematol. Oncol., 7 (1) (1977), pp. 114–134.
Appleton, T. C. and Hall, J. R., Inorganic Chemistry, vol. 11, No. 1, 1972, pp. 112–117.

*Primary Examiner*—Helen M. S. Sneed
*Attorney, Agent, or Firm*—Brumbaugh, Graves, Donohue & Raymond

[57] ABSTRACT

Platinum(IV)-diamine-complexes, a process for the preparation thereof, a process for the preparation of a medicine using such a platinum(IV)-diamine-complex for the treatment of malignant tumors in mice as well as the shaped medicine thus obtained.

This invention relates to novel platinum-diamine complexes, a pharmaceutical composition using the novel complexes and methods of treating malignant tumors in mice using the pharmaceutical composition.

19 Claims, No Drawings

PLATINUM(IV)-DIAMINE COMPLEXES, A PROCESS FOR THE PREPARATION THEREOF, A PROCESS FOR THE PREPARATION OF A MEDICINE USING SUCH A PLATINUM(IV)-DIAMINE COMPLEX FOR THE TREATMENT OF MALIGNANT TUMORS IN MICE

This is a continuation-in-part application of application Ser. No. 213,065 filed Dec. 4, 1980, now abandoned.

The invention relates to new platinum(IV)-diamine complexes, to a process for the preparation thereof, to a process for the preparation of a medicine using such a platinum(IV)-diamine complex for the treatment of malignant tumors in mice, like malignant swellings or malignant tumours, and to a shaped medicine obtained by using this process.

From the literature it is known that platinum-diamine complexes, as well derived from bivalent platinum as from tetravalent platinum are usable for the treatment of cancer. Vide for example the article of B. Rosenberg and L. van Camp, Cancer Research 30 (1970) 1799–1802.

Relevant literature with respect to the use of bivalent platinum-diamine complexes, like the cis-platinum diamine dichloride, for the treatment of cancer is for example the article of A. P. Zipp and S. G. Zipp, J.Chem.Ed., 54 (12) (1977), page 739, which describes the use of cis-platinum diamine dichloride for the treatment of cancer. It is mentioned that the platinum compounds have a broad spectrum as antitumour agents, but also that they have important disadvantages, especially a toxicity for kidneys. As method for counteracting kidney toxicity a combination of the cis-platinum diamine dichloride with another substance or with the use of large amounts of liquid or other techniques to flow the kidneys is proposed.

J.Clinical Hematol, Oncol., 7 (1) (1977), pages 114–134, mentions a large number of platinum-diamine complexes, among which cis-platinum-dichloro diamine, for the treatment of cancer. This article also mentions the kidney toxicity as the most important disadvantage of the compounds.

Also Chem. and Eng. News, June 6, 1977, pages 29–30, describes the cis-platinum diamine dichloride and the use thereof for the treatment of cancer. This article also mentions the kidney toxicity as the most important disadvantage.

From the article in Cancer Chemotherapy Reports Part 1, Vol. 59, No. 3, May/June 1975, pages 629–641 also the kidney toxicity of cis-dichloro diamine platinum(II) appears. Because of this kidney toxicity and also the low therapeutical index thereof other platinum complexes for the treatment of cancer were investigated.

In the non-prepublished Dutch patent applications Nos. 78.07334 and 79.04740 new platinum (II)-diamine complexes are described, which are well suitable for the treatment of cancer and which exhibit a low or no kidney toxicity at all. These applications are dealing with so-called bidentate ligand complexes from bivalent platinum, characterized by formula

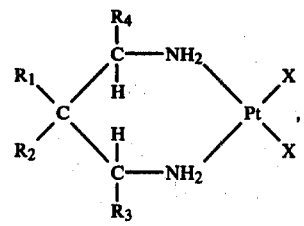

wherein the bidentate ligand is a substituted or not propane diamine. The mentioned compounds exhibit, because of the nature of the substituents $R_1$, $R_2$, $R_3$ and $R_4$ a low or completely no kidney toxicity.

With respect to the use of tetravalent platinum diamine complexes for the treatment of cancer in the literature the following is mentioned.

The above mentioned article from Rosenberg and Van Camp describes for the first time the antitumour activity of a platinum(IV) complex, the cis-platinum-(IV)diamine tetrachloride, illustrated in formula

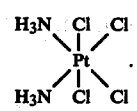

This compound is also discussed by M. L. Tobe and A. R. Khokhar, J.Clinical Hematol.Oncol., 7 (1) (1977), pages 114–134, together with a large number of other platinum(IV)complexes with as monodentate ligands two primary amines, illustrated by formula 3 of the formulae sheet.

Similar complexes are also described in the Dutch patent application No. 78.10431, which also relates to monodentate ligand complexes, characterised by formula

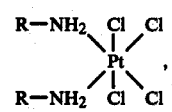

wherein R has the general formula cyclo-$C_nZ_{2n-1}$.

Platinum(IV) complexes with bidentate amine ligands, wherein the amine groups are separated from each other by two carbon atoms (ethylene group), formula

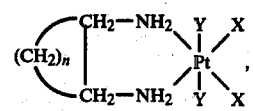

are mentioned in J.Clinical Hematol.Oncol., 7 (1) (1977), pages 231–241, and in Dutch patent application No. 79.03048. Platinum(IV) complexes with bidentate aminoacid ligands, wherein the platinum is partly complexed with nitrogen and partly with oxygen groups, are described in Dutch patent application No. 79.03050.

The present invention relates to new platinum(IV)-diamine complexes, which are characterized by the formula

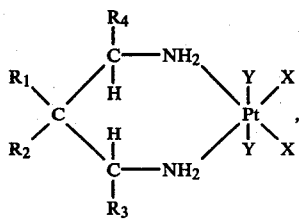

(5)

wherein $R_1$ and $R_2$ independently from each other are a hydrogen atom or a substituted or not alkyl group having 1–20 carbon atoms, a cycloalkyl group having 3–7 carbon atoms, an aryl or aralkyl group having 1–20 carbon atoms in the alkyl group, whereas $R_1$ and $R_2$ together may be a substituted or not cycloalkyl group having 3–7 carbon atoms, $R_3$ and $R_4$ are independently from each other a hydrogen atom or a substituted or not alkyl group having 1–20 carbon atoms, an aryl or aralkyl group having 1–20 carbon atoms in the alkyl group, and X and Y are the same or different anionic groups.

Based on the high anti-tumour activity and the low kidney toxicity compounds having the formula

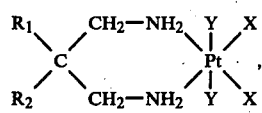

(6)

wherein $R_1$, $R_2$, X and Y have the above meaning, particularly compounds wherein at least one of both groups $R_1$ or $R_2$ have more than one carbon atom, are preferred.

Preferably compounds having the formulae

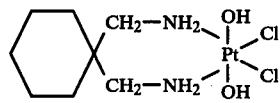

(7)

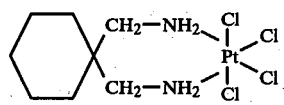

(8)

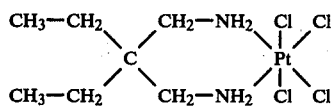

(9)

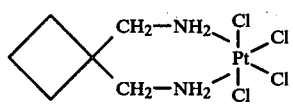

(10)

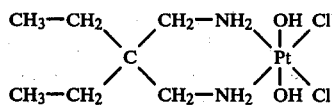

(11)

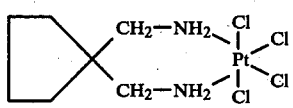

(12)

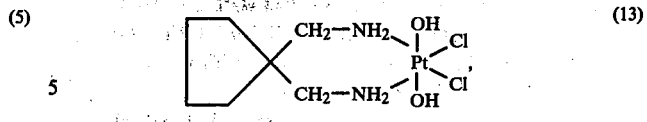

(13)

and most preferably the cis-dichloro-trans-dihydroxy-1,1-bis (aminomethyl)cyclohexane platinum(IV) (formula 7) and the cis-tetrachloro-1,1-bis(aminomethyl)-cyclohexane platinum (VI) (formula 8) are used.

In the formulae 5 and 6 the anionic group X is preferably chlorine, bromine or iodine, a sulphate radical or a substituted or not carboxylate radical, like an acetate or substituted acetate, an oxalate, malonate or substituted malonate group or a 4-carboxyphthalate group, the anionic group Y is (independently from group X) preferably chlorine, bromine or iodine, a hydroxyl group or a nitrate group.

The invention further relates to a process for the preparation in a way known per se of these compounds, to a process for the preparation of a medicine, wherein these compounds are used as active substance, as well as to a shaped medicine so obtained.

Extensive investigation has proved that the compounds according to the invention exhibit a high therapeutical activity against malignant tumor in mice. The results of this investigation are set forth in Table A.

TABLE A

Anti-tumor activity in BDF-1 mice[a]

| Compound | Tumor | Dose/injection (mg/kg) | T/C[e] (%) |
|---|---|---|---|
| cis-DDP[b] | LE[c] | 10 | 186 |
| Formula 7 | " | 16 | 214 |
| Formula 7 | " | 12 | 283 |
| Formula 8 | " | 12 | 236 |
| Formula 9 | " | 8 | 229 |
| Formula 10 | " | 8 | 207 |
| Formula 12 | " | 6 | 257 |
| cis-DDP | LE/cis DDP[d] | 8 | 121 |
| Formula 7 | " | 15 | 229 |
| Formula 8 | " | 6 | 171 |
| Formula 12 | " | 4 | 138 |

[a]For detailed information concerning the test procedure and its interpretation, see Introduction 14, Screening data summary interpretation and outline of current screen, Drug Evaluation Branch, National Cancer Institute, Bethesda, Maryland, 20014, 1977.
[b]Cis-diamminedichloroplatinum(II)
[c]LE = L-1210 lymphoid leukemia
[d]A subline of L-1210 resistant to cis-DDP
[e]Period of survival of the mice treated (T) in relation to untreated mice (C); the therapeutic activity is significant at T/C >125.

Contrary to the platinum complexes known so far and practically used for the combat of cancer, like the cis-platinum diamine chloride (DDP), it appeared from the results set forth in Table B below thereby also that the compounds according to the invention are showing a low or even no kidney toxicity at all.

TABLE B

Percentage of blood urea-nitrogen (BUN) after administering platinum complexes (in the rat)[a].

| Compound | Dose (mg/kg) | Incidence of BUN >30 mg % |
|---|---|---|
| Cis-DDP | 18 | 8/10 |
|  | 13 | 9/10 |
| Formula 7 | 29 | 0/10 |
|  | 16 | 0/10 |
| Formula 8 | 16 | 0/10 |
|  | 9 | 0/10 |
| Formula 9 | 27 | 1/9 |
|  | 15 | 0/10 |
| Formula 10 | 11 | 0/10 |

TABLE B-continued

Percentage of blood urea-nitrogen (BUN) after administering platinum complexes (in the rat)[a].

| Compound | Dose (mg/kg) | Incidence of BUN >30 mg % |
|---|---|---|
|  | 6 | 0/10 |
| Formula 12 | 11 | 1/10 |
|  | 6 | 0/10 |

[a] A generally acknowledged significant method for the determination of kidney toxicity concerns the evaluation of the blood urea-nitrogen; BUN values ≧ 30 mg % are considered indicative of drug-induced nephrotoxicity.

The invention is further illustrated by the following examples.

PREPARATION OF THE PLATINUM COMPLEXES

The complexes are prepared by a general process, wherein first the platinum (II) product is prepared, which is then converted by means of an oxidation agent to the corresponding platinum(IV) compound.

The platinum (II) product with the general formula cis-$LPtCl_2$, wherein L is the diamine (bidentate ligand) in the complex, is prepared according to the method of: G. L. Johnson, Inorg. Synth. VIII, 242–244.

From the desired diamine first the di-HCl-salt is prepared. This is dissolved in water, thereafter the equimolecular amount of $K_2PtCl_4$ is added. The mixture is then heated to 95° C. Now an equimolecular amount of NaOH in water is added so quickly that the PH remains at about 6. The formed light yellow precipitate is filtered, washed with water and dried. The product obtained can be purified by recrystallisation from DMF.

The cis-$LPtCl_2$(II) is converted with chlorine gas to cis-$LPtCl_4$-IV and with hydrogen peroxide (30%) it is oxidized to cis-$LPt$-$(OH)_2Cl_2$(IV).

The conversion to cis-$LPtCl_4$(IV) is described in Inorg. Synth. VII, 236–238, by G. B. Kaufman.

The cis-$LPtCl_2$ is suspended in water and oxidized by passing through at 70°–75° C. chlorine gas during about one hour. Thereafter air is sucked through to remove the excess of chlorine (temperature=70° C., time: 5 minutes). The mixture is cooled, the product is filtered, washed with water and dried under reduced pressure.

The oxidation to cis-$LPt(OH)_2Cl_2$(IV) takes place by boiling a suspension of cis-$LPtCl_2$(II) during 0.5 hour with an excess of 30% $H_2O_2$. The suspension is cooled and the product is filtered, washed with water and dried under reduced pressure.

The conversion of the cis-$LPt(OH)_2Cl_2$(IV) to cis-$LPt$-$Cl_4$(IV) may also be carried out by heating a suspension of the cis-$LPt(OH)_2Cl_2$(IV) during 5 minutes at 100° C. with concentrated hydrochloric acid.

The latter two reactions are described in J. Am. Chem. Soc., 72, 2433 (1950) by F. Basolo, J. C. Bailar jr. and B. Rapp-Tarr, and are slightly modified (boiling of the reaction product instead of heating at 80° C.; the use of 30% $H_2O_2$ instead of 10% $H_2O_2$; excess $H_2O_2$: 50–70 instead of 10).

EXAMPLE I

Cis-dichloro-trans-dihydroxy-1,1-bis-(aminomethyl)cyclohexane platinum(IV) having the formula 7

1,2 g cis-dichloro-1,1-bis(aminomethyl)-cyclohexane platinum(II) is suspended in 5 ml distilled water. 25 ml 30% hydrogen peroxide is added. Stirring is carried out during 0.5 hour at room temperature; thereafter one hour under reflux. The suspension is cooled and the solid substance is filtered, washed with water and dried under reduced pressure. Weight or light yellow solid substance: 0.45 g Analysis (weight %): Calculated: C, 21.73; H, 4.56; H, 6.33; Pt, 44.11; Cl, 16.03. Found: C, 21.78; H, 4.54; H, 6.21; Pt, 43.98; Cl, 15.85.

IR-spectrum(CsI-pill): Pt-Cl 332 cm$^{-1}$; Pt-O 545 cm$^{-1}$.

EXAMPLE II

Cis-tetrachloro-1,1-bis(aminomethyl)-cyclohexane platinum(IV) having the formula 8

1,2 g cis-dichloro-1,1-bis(aminomethyl)cyclohexane platinum(II) is suspended in 15 ml distilled water. The suspension is then heated to 70° C., whereafter under stirring during one hour chlorine gas is introduced. The excess chlorine gas is removed by passing air through the reaction mixture (temperature=70° C.). The reaction mixture is cooled and the solid substance is filtered, washed with water and dried under reduced pressure.

Weight of yellow solid substance: 0.9 g (63%).

Analysis (weight %): Calculated: C, 20.05; H, 3.79; N, 5.85; Pt, 40.72. Found: C, 20.20; H, 3.74; N, 5.88; Pt, 40.90.

$^1$H—NMR spectrum in DMSO-d6 (Varian-T 60)

| $CH_2$ (ring) | 1.35 ppm | |
|---|---|---|
| $CH_2$ ($NH_2$) | 2.23 ppm | |
| $NH_2$ | 6.30 ppm | with respect to TMS |
|  | 6.80 ppm | |
|  | 7.27 ppm | |

IR-spectrum (CsI-pill): Pt-Cl 332–350 cm$^{-1}$.

EXAMPLE III

Cis-tetrachloro-2,2-diethyl-1,3-diaminopropane platinum(IV) having the formula 9

This complex was prepared in an analogous way as in Example II starting from 1.6 g cis-dichloro-2,2-diethyl-1,3-diaminopropane platinum(II).

Yield: 1.5 g (79%).

Analysis (weight %): Calculated: C, 18.00; H, 3.88; N, 6.00; Pt, 41.76. Found: C, 18.25; H, 3.90; N, 6.32; Pt, 41.21.

$^1$H—NMR-spectrum in DMSO-d6 (Varian-T 60)

| $CH_3$ (Et) | 0.73 ppm | |
|---|---|---|
| $CH_2$ (Et) | 1.23 ppm | |
| $CH_2$ ($NH_2$) | 2.20 ppm | |
| $NH_2$ | 6.18 ppm | with respect to TMS |
|  | 6.70 ppm | |
|  | 7.15 ppm | |

IR-spectrum (CsI-pill): Pt-Cl 343 cm$^{-1}$.

EXAMPLE IV

Cis-tetrachloro-1,1-bis(aminomethyl)cyclobutane platinum(IV) having the formula 10

This product was prepared in an analogous way as in Example II. Starting from 1.14 g cis-dichloro-1,1-bis-(aminomethyl)cyclobutane platinum(II) 1.2 g (88%) of the desired product was isolated.

Analysis (weight %): Calculated: C, 15.98; H, 3.13; N, 6.21; Pt, 43.25. Found: C, 16.06; H, 3.07; N, 6.23; Pt, 43.35.

$^1$H—NMR-spectrum in DMSO-d6 (Varian-T 60)

| | | |
|---|---|---|
| CH$_2$ ring | 1.82 ppm | |
| CH$_2$ (NH$_2$) | 2.40 ppm | |
| NH$_2$ | 6.30 ppm | with respect to TMS |
| | 6.78 ppm | |
| | 7.30 ppm | |

IR-spectrum (CsI-pill): Pt-Cl: 350 cm$^{-1}$.

EXAMPLE V

Cis-dichloro-trans-dihydroxy-2,2-diethyl-1,3-diaminopropane platinum(IV) having the formula 11

This complex was prepared in an analogous way as in Example I starting from 1.5 g cis-dichloro-2,2-diethyl-1,3-diaminopropane platinum(II).

Yield: 0.95 g (58%).

Analysis (weight %): Calculated: C, 19.54; H, 4.69; N, 6.51; Pt, 45.34; Cl, 16.48. Found: C, 19.62; H, 4.8; N, 6.3; Pt, 45.5; Cl, 16.4.

IR-spectrum (CsI-pill): Pt-Cl: 343 cm$^{-1}$; Pt-O: 542 cm$^{-1}$.

EXAMPLE VI

Cis-tetrachloro-1,1-bis(aminomethyl)-cyclohexane platinum(IV) having the formula 8

Cis-dichloro-trans-dihydroxy-1,1-bis(aminomethyl) cyclohexane platinum(IV) was prepared as in Example I, whereafter hydrochloric acid was added to the obtained suspension. After heating during 5 minutes at 95°-100° C. the reaction mixture was cooled. The product was filtered and washed with water.

The compound was characterized in that the 'H—NMR— as well as the IR-spectrum appeared to be identical to the spectra of Example II.

EXAMPLE VII

Cis-tetrachloro-1,1-bis(aminomethyl)cyclopentane platinum(IV) having the formula 12

This complex was prepared in an analogous way as in Example II, starting from 1.6 g cis-dichloro-1,1-bis-(aminomethyl)cyclopentane platinum(II).

Yield: 1.3 g (69%).

Analysis (weight %): Calculated: C, 18.08; H, 3.47; N, 6.02; Pt, 41.94. Found: C, 18.20; H, 3.48; N, 6.09; Pt, 42.11.

| 'H—NMR spectrum in DMSO-d6 (Varian-T 60) | | |
|---|---|---|
| CH$_2$ (ring) | 1.50 ppm | |
| CH$_2$ (NH$_2$) | 2.23 ppm | |
| NH$_2$ | 6.33 ppm | with respect to TMS |
| | 6.80 ppm | |
| | 7.20 ppm | |

IR-spectrum (CsI-pill): Pt-Cl 342 cm$^{-1}$.

EXAMPLE VIII

Cis-dichloro-trans-dihydroxy-1,1-bis(aminomethyl)cyclopentane platinum(IV) having the formula 13

This complex was prepared in an analogous way as in Example I starting from 1.2 g cis-dichloro-1,1-bis-(aminomethyl)cyclopentane platinum(II).

Yield: 0.6 g (47%).

Analysis (weight %): Calculated: C, 19.63; H, 4.24; N, 6.54; Pt, 45.56; Cl, 16.56. Found: C, 19.54; H, 4.11; N, 6.66; Pt, 45.47; Cl, 16.49.

IR-spectrum (CsI-pill): Pt-Cl 330–345 cm$^{-1}$; Pt-O 540 cm$^{-1}$.

We claim:

1. Platinum(IV)-diamine complexes having the formula:

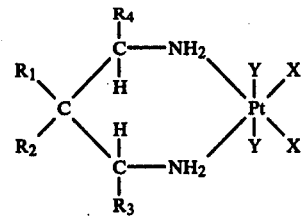

wherein R$_1$ and R$_2$ are independently from each other a hydrogen atom or an alkyl, aryl or aralkyl group having 1–20 carbon atoms or a cycloalkyl group having 3–7 carbon atoms, while R$_1$ and R$_2$ together may be a cycloalkyl group having 3–7 carbon atoms, R$_3$ and R$_4$ are independently from each other a hydrogen atom or alkyl, aryl, aralkyl group having 1–20 carbon atoms and X and Y are independently from each other an anionic group, provided that when X and Y are both chlorine or when X is chlorine and Y is hydroxy R$_1$, R$_2$, R$_3$ and R$_4$ are not each hydrogen; when X and Y are both chlorine and R$_1$ and R$_2$ are both hydrogen, R$_3$ and R$_4$ are not each methyl and when X and Y are both chlorine and R$_1$ and R$_2$ are both methyl R$_3$ and R$_4$ are not each hydrogen.

2. The platinum(IV)-diamine complex as described in claim 1 wherein R$_3$ and R$_4$ are both hydrogen.

3. Cis-dichloro-trans-dihydroxy-1,1-bis (aminomethyl) cyclohexane platinum(IV) having the formula:

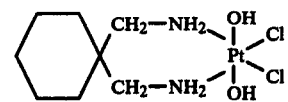

4. Cis-tetrachloro-1,1-bis(aminomethyl) cyclohexane platinum(IV) having the formula:

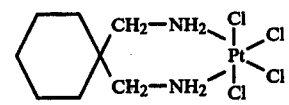

5. Cis-tetrachloro-2,2-diethyl-1,3-diaminopropane platinum(IV) having the formula:

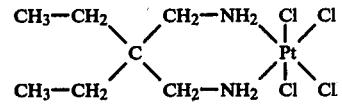

6. Cis-tetrachloro-1,1-bis(aminomethyl) cyclobutane platinum(IV) having the formula:

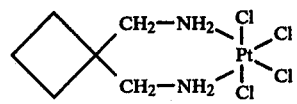

7. Cis-dichloro-trans-dihydroxy-2,2-diethyl-1,3-diamonopropane platinum(IV) having the formula:

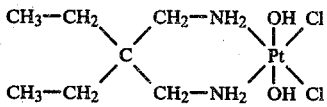

8. Cis-tetrachloro-1,1-bis(aminomethyl) cyclopentane platinum(IV) having the formula:

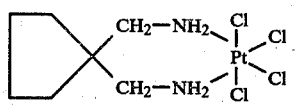

9. Cis-dichloro-trans-dihydroxy-1,1-bis (aminomethyl) cyclopentane platinum(IV) having the formula:

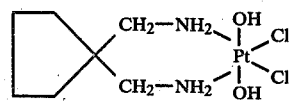

10. Pharmaceutical composition comprising a suitable carrier and an amount sufficient to treat malignant tumors in mice of at least one of the platinum(IV) diamine complexes having the formula:

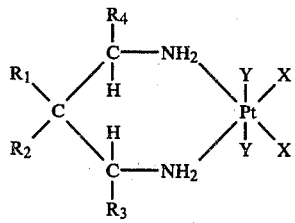

wherein $R_1$ and $R_2$ are independently from each other a hydrogen atom or an alkyl, cycloalkyl, aryl or aralkyl group, while $R_1$ and $R_2$ together may be a cycloalkyl group, $R_3$ and $R_4$ are independently from each other a hydrogen atom or alkyl, aryl, aralkyl group and X and Y are independently from each other an anionic group, provided that when X and Y are both chlorine and $R_1$ and $R_2$ are both methyl, $R_3$ and $R_4$ are not each hydrogen.

11. A pharmaceutical composition comprising a suitable carrier and an amount of the compound described in claim 3 sufficient to treat malignant tumors in mice.

12. A pharmaceutical composition comprising a suitable carrier and an amount of the compound described in claim 4 sufficient to treat malignant tumors in mice.

13. A pharmaceutical composition comprising a suitable carrier and an amount of the compound described in claim 5 sufficient to treat malignant tumors in mice.

14. A pharmaceutical composition comprising a suitable carrier and an amount of the compound described in claim 6 sufficient to treat malignant tumors in mice.

15. A pharmaceutical composition comprising a suitable carrier and an amount of the compound described in claim 7 sufficient to treat malignant tumors in mice.

16. A pharmaceutical composition comprising a suitable carrier and an amount of the compound described in claim 8 sufficient to treat malignant tumors in mice.

17. A pharmaceutical composition comprising a suitable carrier and an amount of the compound described in claim 9 sufficient to treat malignant tumors in mice.

18. A method for treating malignant tumors in mice which consists of administering a therapeutically effective amount of the composition as described in claim 1, 2, 3, 4, 5, 6, 7, 8 or 9 to mice having malignant tumors.

19. A method of treating malignant tumors in mice which consists of administering a therapeutically effective amount of the composition as described in claim 10.

* * * * *

UNITED STATES PATENT AND TRADEMARK OFFICE
CERTIFICATE OF CORRECTION

PATENT NO.   : 4,431,666

DATED        : February 14, 1984

INVENTOR(S)  : Eric J. Bulteb et al.

It is certified that error appears in the above-identified patent and that said Letters Patent is hereby corrected as shown below:

Column 10, line 42, "method for" should read -- method of --.

Signed and Sealed this

Fourth Day of June 1985

[SEAL]

Attest:

DONALD J. QUIGG

Attesting Officer       Acting Commissioner of Patents and Trademarks